United States Patent [19]
Häbich et al.

[11] Patent Number: 5,861,413
[45] Date of Patent: Jan. 19, 1999

[54] 2-OXO- AND 2-THIO-1,2-DIHYDROQUINOLINYL-OXAZOLIDINONES

[75] Inventors: Dieter Häbich; Andreas Stolle; Bernd Riedl; Martin Ruppelt, all of Wuppertal; Stephan Bartel, Bergisch Gladbach; Walter Guarnieri, Zülpich; Rainer Endermann; Hein-Peter Kroll, both of Wuppertal, all of Germany

[73] Assignee: Bayer Aktiengesellschaft, Leverkusen, Germany

[21] Appl. No.: 781,002

[22] Filed: Jan. 9, 1997

[30] Foreign Application Priority Data

Jan. 16, 1996 [DE] Germany .................. 196 01 265.1

[51] Int. Cl.$^6$ .................. A61K 31/47; C07D 413/04
[52] U.S. Cl. .................. 514/312; 546/157
[58] Field of Search .................. 546/157; 514/312

[56] References Cited

U.S. PATENT DOCUMENTS

| | | |
|---|---|---|
| 4,705,799 | 11/1987 | Gregory . |
| 4,801,600 | 1/1989 | Wang et al. . |
| 4,942,183 | 7/1990 | Gregory et al. . |
| 4,965,268 | 10/1990 | Wang et al. . |
| 5,164,510 | 11/1992 | Brickner . |
| 5,254,577 | 10/1993 | Carlson et al. . |
| 5,475,014 | 12/1995 | Akasaka et al. . |
| 5,561,148 | 10/1996 | Gante et al. . |
| 5,574,055 | 11/1996 | Borgulya et al. . |

OTHER PUBLICATIONS

C. Pak et al., J.Med.Chem., vol. 35, pp. 1156–1165 (1992).

J. Swenson et al., Antimicrobial Agents and Chemitherapy, vol. 22, No. 2, pp. 186–192 (1982)AR.

*Primary Examiner*—Patricia L. Morris
*Attorney, Agent, or Firm*—Sprung Kramer Schaefer & Briscoe

[57] ABSTRACT

The present invention relates to 2-oxo- and 2-thio-1,2-dihydroquinolinyl-oxazolidinones, processes for their preparation and their use as medicaments, in particular as antibacterial medicaments.

6 Claims, No Drawings

2-OXO- AND 2-THIO-1,2-DIHYDROQUINOLINYL-OXAZOLIDINONES

The present invention relates to 2-oxo- and 2-thio-1,2-dihydroquinolinyl-oxazolidinones, processes for their preparation and their use as medicaments, in particular as antibacterial medicaments.

N-Aryloxazolidinones having antibacterial action are disclosed, for example, in the publication EP 311 090.3-(Nitrogen-substituted)phenyl-5-beta-amidomethyloxazolidin-2-ones are additionally disclosed in EP 609 905 A1.

Furthermore, oxazolidinone derivatives having a monoamine oxidase-inhibitory action are published in WO 93 08 179 A and oxazolidinone derivatives having action as adhesion receptor antagonists are published in EP 645 376.

The present invention relates to 2-oxo- and 2-thio-1,2-dihydroquinolinyl-oxazolidinones of the general formula (I)

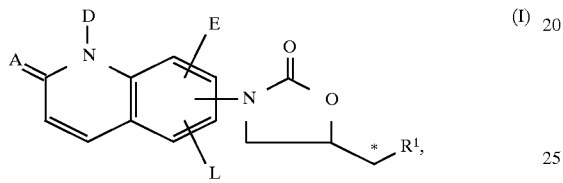

in which
A represents an oxygen or a sulphur atom,
D represents hydrogen or cycloalklyl having 3 to 6 carbon atoms, or represents straight-chain or branched alkoxycarbonyl having up to 4 carbon atoms, or represents straight-chain or branched alkyl or alkenyl each having up to 9 carbon atoms, which is optionally substituted by cyano, trifluoromethyl, halogen, hydroxyl, pyridyl, phenyl, carboxyl, carboxamido, straight-chain, or branched alkoxycarbonyl having up to 5 carbon atoms, naphthyl, cycloalkyl having 3 to 6 carbon atoms, and/or by a group of the formula

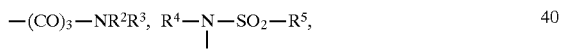

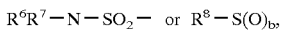

in which
a denotes a number 0 or 1,
$R^2$, $R^3$, $R^4$, $R^6$ and $R^7$ are identical or different and denote hydrogen, straight-chain or branched alkyl having up to 5 carbon atoms or phenyl, or
$R^2$ and $R^3$, together with the nitrogen atom, form a morpholinyl, thiomorpholinyl, pyrrolidinyl, piperazinyl or piperidyl ring, each of which is optionally substituted, also via the free N function, by straight-chain or branched alkyl or acyl each having up to 4 carbon atoms,
b denotes a number 0, 1 or 2,
$R^5$ and $R^8$ are identical or different and denote straight-chain or branched alkyl having up to 6 carbon atoms, benzyl, phenyl or tolyl, or
D represents straight-chain or branched acyl having up to 5 carbon atoms, which is optionally substituted by triflouromethyl, trichloromethyl or a group of the formula —$OR^9$,
in which
$R^9$ denotes hydrogen or straight-chain or branched alkyl having up to 5 carbon atoms, which is optionally substituted by phenyl or naphthyl, or D represents a group of the formula —$(CT)_d$—$NR^{10}R^{11}$, —$(CO)_e$—$NR^{12}$—CO—$NR^{13}R^{14}$, —$NR^{15}$—$SO_2R^{16}$, $R^{17}R^{18}$—N—$SO_2$—, $R^{19}$—$S(O)_f$ or —CO—$R^{20}$,
in which
T denotes an oxygen or sulphur atom,
d and e are identical or different and have the meaning of a indicated above and are identical to or different from this,
$R^{10}$, $R^{11}$, $R^{12}$, $R^{13}$, $R^{14}$, $R^{15}$, $R^{17}$ and $R^{18}$ have the meaning of $R^2$, $R^3$ and $R^4$ in each case indicated above and are identical to or different from this,
f has the meaning of b indicated abone and is identical to or different from this,
$R^{16}$ and $R^{19}$ are identical or different and have the meaning of $R^5$ and $R^8$ indicated above,
$R^{20}$ denotes aryl having 6 to 10 carbon atoms, which is optionally substituted by halogen,
E and L are identical or different and represent hydrogen, carbon, halogen, cyano, formyl trifluoromethyl, nitro, or represents straight-chlain or branched alkyl having up to 4 carbon atoms.
$R^1$ represents azido, hydroxyl or a group of the formula —$OR^{21}$, O—$SO_2R^{22}$ or —$NR^{23}R^{24}$,
in which
$R^{21}$ denotes straight-chain or branched acyl having up to 6 carbon atoms or a hydroxyl protective group,
$R^{22}$ denotes straight-chain or branched acyl having up to 5 carbon atoms, phenyl or tolyl,
$R^{23}$ and $R^{24}$ are identical or different and denote cycloalkyl having, 3 to 6 carbon atoms, hydrogen, phenyl or straight-chain or branched alkooxy having up to 6 carbon atoms, tert-butoxycarbonyl, fluorenyloxycarbonyl or benzyloxycarbonyl, or denote straight-chain or branched alkyl having up to 6 carbon atoms, which is optionally substituted by cyano or alkoxycarbonyl having up to 4 carbon atoms, or
$R^{23}$ and/or $R^{24}$ denotes a group of the formula —CT'—$R^{25}$, $P(O)(OR^{26})(OR^{27})$ or —$SO_2$—$R^{28}$,
in which
T' has the meaning of T indicated above and is identical to or different from this,
$R^{25}$ denotes cycloalkyl having 3 to 6 carbon atoms, trifluoromethyl or straight-chain or branched alkoxy having up to 6 carbon atoms, phenol, benzyloxy or hydrogen, or denotes straight-chain or branched alklyl having up to 6 carbon atoms, which is optionally substituted by straight-chain or branched alkoxycarbonyl having up to 5 carbon atoms, cyano, fluorine, chlorine, bromine or trifluoromethyl, or denotes straight-chain or branched thioalkyl or acyl each having up to 5 carbon atoms, or denotes a group of the formula —$NR^{29}R^{30}$,
in which
$R^{29}$ and $R^{30}$ are identical or different and denote hydrogen, phenyl or straight-chain or branched alkyl having up to 4 carbon atoms, or
$R^{26}$ and $R^{27}$ are identical or different and denote hydrogen or straight-chain or branched alkyl having up to 4 carbon atoms,
$R^{28}$ denotes straight-chain or branched alkyl having up to 4 carbon atoms or phenyl,
and their salts and isomers.

Physiologically acceptable salts of the oxazolidinones according to the invention can be salts with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which may be mentioned are furthermore salts with customary bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

Reaction products with $C_1$–$C_4$-alkyl halides, in particular $C_1$–$C_4$-alkyl iodides, can additionally function as salts.

The compounds according to the inention can exist in stereoisomeric forms which behave either as image and mirror image (enantiomers), or which do not behave as image and mirror image (diastereomers). The invention relates both to the enantiomers or diastereomers or to their respective mixtures. Like the diastereomers, the racemic forms can be separated into the stereoisomerically uniform constituents in a known manner.

Preferred compounds of the general formula (I) are those in which

A represents an oxygen or a sulphur atom,

D represents hydrogen, cyclopropyl, cyclopentyl or cyclohexyl, or represents straight-chain or branched alkoxycarbonyl having up to 3 carbon atoms, or represents straight-chain or branched alkyl or alkenyl each having up to 6 carbon atoms, which is optionally substituted by cyano, trifluoromethyl, fluorine, chlorine, bromine, hydroxyl, pyridyl, phenyl, carboxyl, carboxamido, straight-chain or branched alkoxycarbonyl having up to 4 carbon atoms, naphthyl, cyclopropyl, cyclopentyl or cyclohexyl and/or by a group of the formula —$(CO)_a$—$NR^2R^3$, $R^4$—N—$SO_2$—$R^5$, $R^6R^7$—N—$SO_2$— or $R^8$—$S(O)_b$, in which a denotes a number 0 or 1, $R^2$, $R^3$, $R^4$, $R^6$ and $R^7$ are identical or different and denote hydrogen, straight-chain or branched alkyl having up to 3 carbon atoms or phenyl, or $R^2$ and $R^3$, together with the nitrogen atom, form a morpholinyl, thiomorpholinyl, pyrrolidinyl, piperazinyl or piperidyl ring, each of which is optionally substituted, also via the free N function, by straight-chain or branched alkyl or acyl each having up to 3 carbon atoms, b denotes a number 0, 1 or 2, $R^5$ and $R^8$ are identical or different and denote straight-chain or branched alkyl having up to 4 carbon atoms, benzyl, phenyl or tolyl, or D represents straight-chain or branched acyl having up to 4 carbon atoms, which is optionally substituted by trifluoromethyl, trichloromethyl or a group of the formula —$OR^9$, in which $R^9$ denotes hydrogen or straight-chain or branched alkyl having up to 4 carbon atoms, which is optionally substituted by phenyl or naphthyl, or D represents a group of the formula —$(CT)_d$—$NR^{10}R^{11}$, —$(CO)_e$—$NR^{12}$—CO—$NR^{13}R^{14}$, —$NR^{15}$—$SO_2R^{16}$, $R^{17}R^{18}$—N—$SO_2$—, $R^{19}$—$S(O)_f$ or —CO—$R^{20}$, in which denotes an oxyen or sulphur atom, d and e are identical or different and have the meaning of a indicated above and are identical to or different from this, $R^{10}$, $R^{11}$, $R^{12}$, $R^{13}$, $R^{14}$, $R^{15}$, $R^{17}$ and $R^{18}$ have the meaning of $R^2$, $R^3$ and $R^4$ in each case indicated above and are identical to or different from this, f has the meaning of b indicated above and is identical to or different from this, $R^{16}$ and $R^{19}$ are identical or different and have the meaning of $R^5$ and $R^8$ indicated above, $R^{20}$ denotes phenyl or naphthyl, which is optionally substituted by fluorine, chlorine or bromine, E and L are identical or different and represent hydrogen, fluorine, chlorine, bromine, cyano, methyl or trifluoromethyl, $R^1$ represents azido, hydroxyl or a group of the formula —$OR^{21}$, O—$SO_2R^{22}$ or —$NR^{23}R^{24}$, in which $R^{21}$ denotes straight-chain or branched acyl having up to 5 carbon atoms or benzyl, $R^{22}$ denotes straight-chain or branched alkyl having up to 4 carbon atoms, phenyl or tolyl, $R^{23}$ and $R^{24}$ are identical or different and denote cyclopropyl, cyclopentyl, cyclohexyl, hydrogen, phenyl or straight-chain or branched alkoxy having up to 5 carbon atoms, tert-butoxycarbonyl or benzyloxycarbonyl, or denote straight-chain or branched alkyl having up to 4 carbon atoms which is optionally substituted by cyano or by straight-chain or branched alkoxycarbonyl having up to 3 carbon atoms, or $R^{23}$ and/or $R^{24}$ denotes a group of the formula —CT'—$R^{25}$, $P(O)(OR^{26})(OR^{27})$ or —$SO_2$—$R^{28}$, in which T' has the meaning of T indicated above and is identical to or different from this, $R^{25}$ denotes cyclopropyl, cyclopentyl, cyclohexyl, trifluoromethyl or straight-chain or branched alkoxy having up to 5 carbon atoms, phenyl, benzyloxy or hydrogen, or denotes straight-chain or branched alkyl having up to 5 carbon atoms, which is optionally substituted by straight-chain or branched alkoxycarbonyl having up to 4 carbon atoms, cyano, fluorine, chlorine, bromine or trifluoromethyl, or denotes straight-chain or branched thioalkyl or acyl each having up to 4 carbon atoms, or denotes a group of the formula —$NR^{29}R^{30}$, in which $R^{26}$ and $R^{30}$ are identical or different and denote hydrogen, phenyl or straight-chain or branched alkyl having up to 3 carbon atoms, $R^{26}$ and $R^{27}$ are identical or different and denote hydrogen or straight-chain or branched alkyl having up to 3 carbon atoms, $R^{28}$ denotes straight-chain or branched alkyl having up to 3 carbon atoms or phenyl, and their salts and isomers.

Particularly preferred compounds of the general formula (I) are those in which

A represents an oxygen or a sulphur atom,

D represents hydrogen, cyclopropyl, cyclopentyl, cyclohexyl, allyl or straight-chain or branched alkyl having up to 5 carbon atoms, which is optionally substituted by cyano, hydroxyl, trifluoromethyl, fluorine, chlorine, phenyl, carboxyl, carboxamido, straight-chain or branched alkoxycarbonyl having up to 3 carbon atoms, cyclopropyl, cyclopentyl or cyclohexyl and/or by a group of the formula $-(CO)_a-NR^2R^3$, $R^4-N-SO_2-R^5$, $R^6R^7N-SO_2-$ or $R^8-S(O)_b$,
in which
a denotes a number 0 or 1,
$R^2$, $R^3$, $R^4$, $R^6$ and $R^7$ are identical or different and denote hydrogen or methyl,
b denotes a number 0, 1 or 2,
$R^5$ and $R^8$ are identical or different and denote straight-chain or branched alkyl having up to 3 carbon atoms, benzyl, phenyl or tolyl, or D represents a Group of the formula $-(CT)_d-NR^{10}R^{11}$, $-(CO)_e-NR^{12}-CO-NR^{13}R^{14}$, $-NR^{15}-SO_2R^{16}$, $R^{17}R^{18}N-SO_2-$, $R^{19}-S(O)_f$ or $-CO-R^{20}$,
in which
T denotes an oxygen or sulphur atom,
d and e are identical or different and have the meaning of a indicated above and are identical to or different from this,
$R^{10}$, $R^{11}$, $R^{12}$, $R^{13}$, $R^{14}$, $R^{15}$, $R^{17}$ and $R^{18}$ have the meaning of $R^2$, $R^3$ and $R^4$ in each case indicated above and are identical to or different from this,
f has the meaning of b indicated above and is identical to or different from this,
$R^{16}$ and $R^{19}$ are identical or different and have the meaning of $R^5$ and $R^8$ indicated above,
$R^{20}$ denotes phenyl or naphthyl, which is optionally substituted by fluorine, chlorine or bromine, E and L are identical or different and represent hydrogen or fluorine,
$R^1$ represents azido, hydroxyl or a group of the formula $-OR^{21}$, $O-SO_2R^{22}$ or $-NR^{23}R^{24}$,
in which
$R^{21}$ denotes straight-chain or branched acyl having up to 4 carbon atoms,
$R^{22}$ denotes methyl or tolyl,
$R^{23}$ and $R^{24}$ are identical or different and denote cyclopropyl, hydrogen, phenyl or straigiht-chain or branched alkoxy having up to 4 carbon atoms, tert-butoxycarbonyl or benzyloxycarbonyl, or denote straight-chain or branched alkyl having up to 3 carbon atoms, which is optionally substituted by cyano or methoxycarbonyl, or
$R^{23}$ and/or $R^{24}$ denotes a group of the formula $-CT'-R^{25}$,
in which
T' has the meaning of T indicated above and is identical to or different from this,
$R^{25}$ denotes cyclopropyl, cyclclopentyl, cyclohexyl, trifluoromethyl or straight-chain or branched alkoxy having up to 4 carbon atoms, phenyl, benzyloxy or hydrogen, or denotes straight-chain or branched alkyl having up to 4 carbon atoms, which is optionally substituted by straight-chain or branched alkoxycarbonyl having up to 3 carbon atoms, cyano, fluorine, chlorine, bromine or trifluoromethyl, or denotes straight-chain or branched thioalkyl or acyl each having up to 3 carbon atoms, or denotes a group of the formula $-NR^{29}R^{30}$,
in which
$R^{29}$ and $R^{30}$ are identical or different and denote hydrogen, phenyl, methyl or ethyl, and their salts and isomers.

Very particularly preferred compounds of the general formula (I) are those in which E and L represent hydrogen and the oxazolidinone radical is bonded to the 1,2-dihydroquinolinyl ring in position 6 or 7.

Processes for the preparation of the compounds of the general formula (I) according to the invention have additionally been found, characterized in that

[A] N-oxides of the general formula (II)

(II)

in which

E and L have the meaning indicated above and
$R^1$ has the meaning indicated above, but preferably represents the radical of the formula $-NH-CO-NR^{31}$,
in which
$R^{31}$ denotes straight-chain or branched alkyl having up to 4 carbon atoms, are first converted by reaction with $Ac_2O$ or $p$-$TsCl/K_2CO_3$ in inert solvents into the compounds of the general formula (Ia)

(Ia)

in which $R^1$, E and L have the meaning indicated above and
A' represents oxygen, or

[B] compounds of the general formula (Ib)

(Ib)

in which

E and L have the meaning indicated above
and $R^{31}$ represents $C_1$–$C_4$-acyl or alkoxycarbonyl, are reacted vith alkylating agents of the general formula (III)

$$D'-X \qquad (III),$$

in which

D' has the meaning indicated above but does not represent hydrogen and
X represents trifluoromethanesulphonate or halogen, in inert solvents and in the presence of a base, and, if appropriate, the other substituents mentioned under $R^1$ are introduced by customary methods, or

[C] compounds of the general formula (IV)

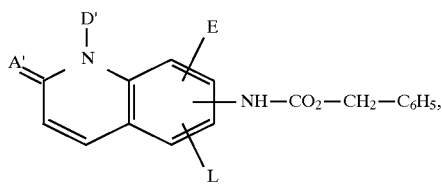

in which

A', D', E and L have the meaning indicated above,
are first converted by reaction with lithium alkyls in ethers and R-glycidyl butyrate of the formula (V)

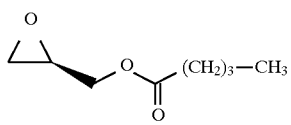

into the compounds of the general formula (Ic)

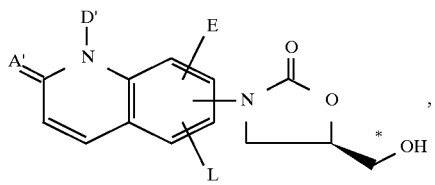

in which

A', D', E and L have the meaning indicated above,
which are converted by reaction with ($C_1$–$C_4$)-alklyl or phenylsulphonyl chlorides in inert solvents and in the presence of a base into the corresponding compounds of the general formula (Id)

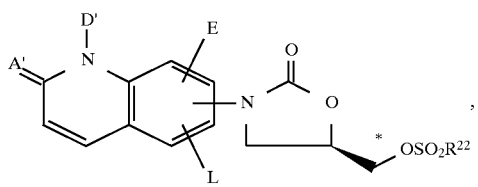

in which

A', D', E, L and $R^{22}$ have the meaning indicated above, then, using sodium azide in inert solvents, the azides of the general formula (Ie)

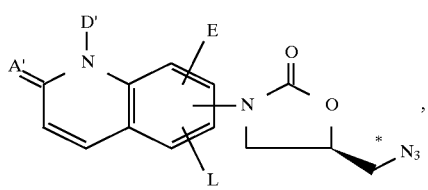

in which

A', D', E and L have the meaning indicated above, are prepared, which are converted in a further step by reaction with alkyl phosphites or $PPh_3$, preferably $(CH_3O)_3P$, in inert solvents and with acids into the amines of the general formula (If)

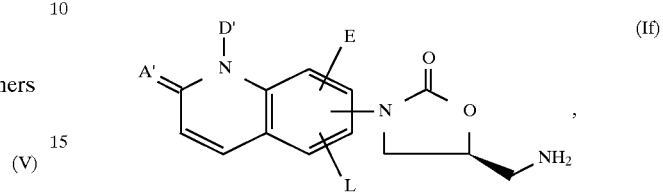

in which

A', D', E and L have the meaning indicated above, and by reaction with acetic anhydride or other acylating agents of the general formula (VI)

in which $R^{25}$ and T' have the meaning indicated and $R^{32}$ represents halogen, preferably chlorine or the radical —$OCOR^{25}$, in inert solvents the compounds of the general formula (Ig)

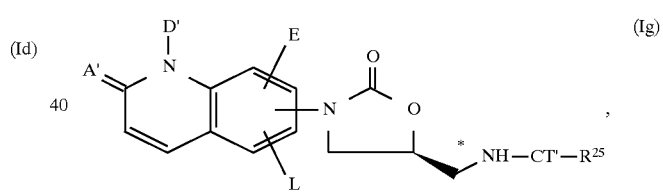

in which

A', D', E, L, T' and $R^{25}$ have the meaning indicated above are prepared, and if A=S, for example, compounds of the general formula (Ig) are subjected to a sulphurization of the amide function using Lawesson's reagent or $P_2S_5$ in toluene or 1,2-dimethoxyethane.

The process variants according to the invention can be illustrated by way of example by the following reaction scheme:

[A]
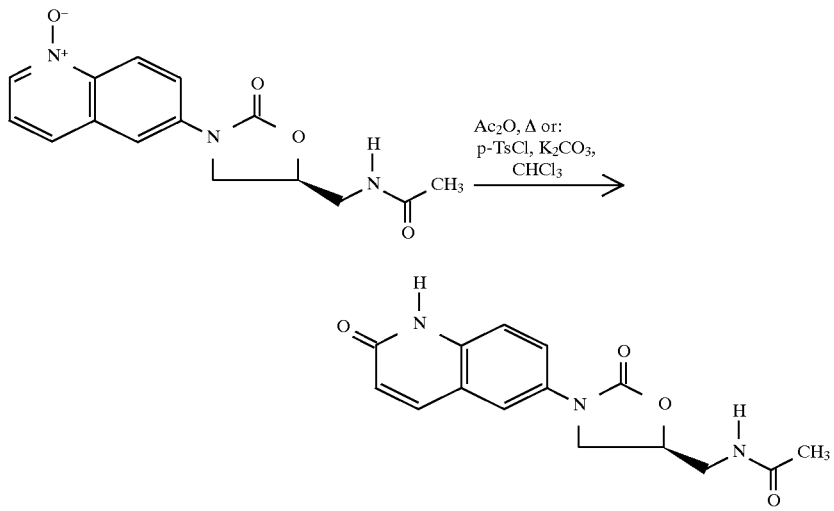
[B]
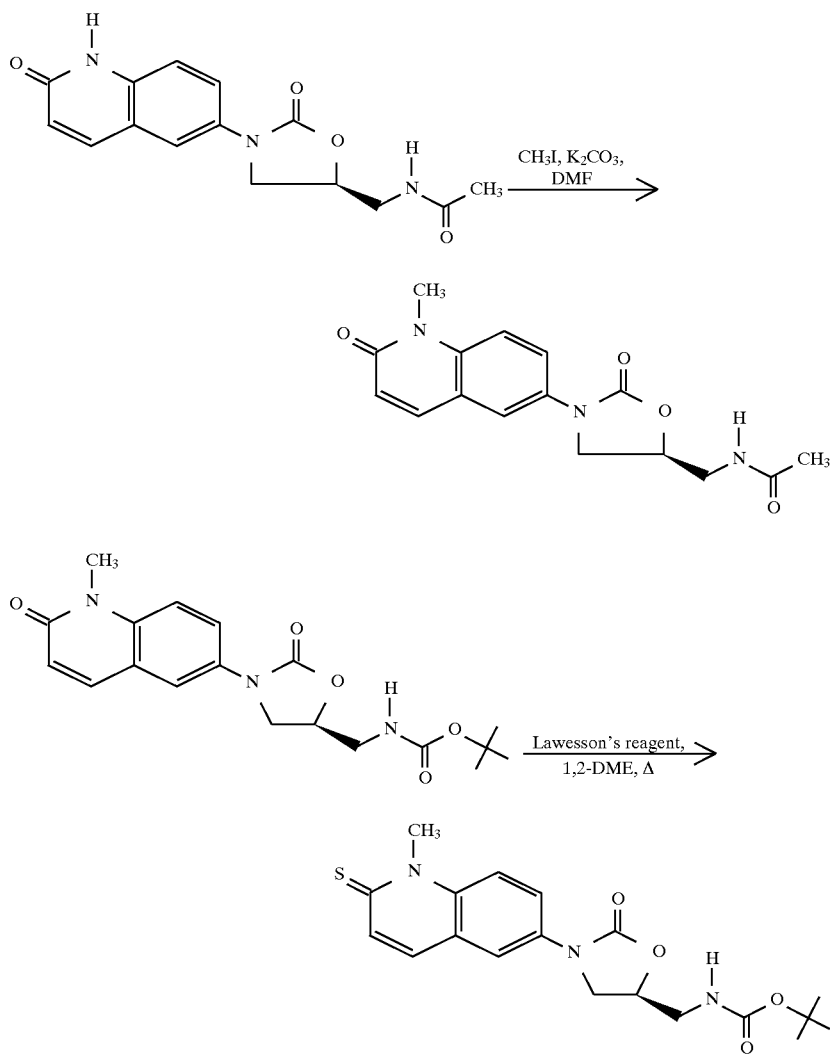

[C]

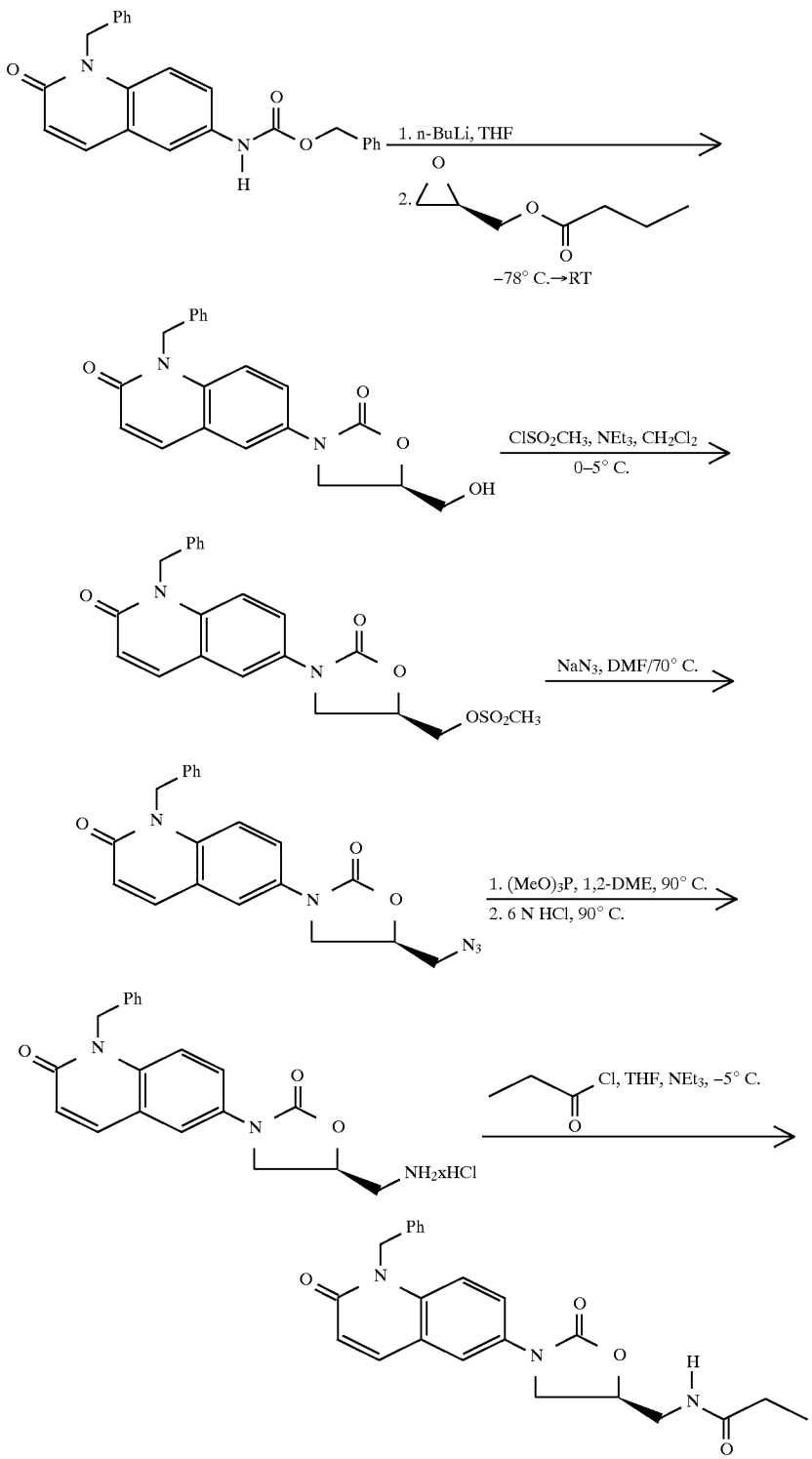

Suitable solvents, depending on the individual process steps, are the customary solvents which do not change under the reaction conditions. These preferably include alcohols such as methanol, ethanol, propanol or isopropanol, or ethers such as diethyl ether, dioxane, 1,2-dimethoxyethane, tetrahydrofuran, glycol dimethyl ether or tert-butyl methyl ether, or ketones such as acetone or butanone, or amides such as dimethylformamide or hexamethylphosphoramide, or hydrocarbons such as hexane, benzene, dichlorobenzene, xylene or toluene, or dimethyl sulphoxide, acetonitrile, ethyl acetate, or halohydrocarbons such as methylene chloride, chloroform or carbon tetrachloride, or pyridine, picoline or N-methylpiperidine. Mixtures of the solvents mentioned can also be used.

Suitable bases, depending on the individual process steps, are the customary inorganic or organic bases. These preferably include alkali metal hydroxides such as, for example, sodium or potassium hydroxide, or alkali metal carbonates such as sodium or potassium carbonate, or alkali metal alkoxides such as, for example, sodium or potassium methoxide, or sodium or potassium ethoxide, or organic amines such as ethyldiisopropylamine, triethylamine, picoline, pyridines or N-methylpiperidine, or amides such as sodium amide or lithium diisopropylamide, or lithium N-silyalkylamides, such as, for example, lithium N-(bis) triphenylsilylamide or lithium alkyls such as n-butyllithium.

The base is employed in an amount of from 1 mol to 10 mol, preferably from 1 mol to 3 mol, based on 1 mol of the compounds of the general formulae (I$b$), (II), (III) and (IV).

All reactions are in general carried out at normal, elevated or at reduced pressure (e.g. 0.5 to 5 bar). In general, the reactions are carried out at normal pressure.

Suitable solvents for the alkylation are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, acetonitrile, acetone or nitromethane. It is also possible to use mixtures of the solvents mentioned. Acetonitrile, dimethyl sulphoxide and dimethylformamide are preferred.

The alkylation is carried out in the abovementioned solvents at temperatures of from 0° C. to +150° C., preferably at room temperature to +100° C., at normal pressure.

The first step of the process [B] takes place in one of the abovementioned ethers using lithium alkyl compounds or lithium N-silylamides, such as, for example, n-butyllithium, lithium diisopropylamide or lithium bistrimethylsilylamide, preferably in tetrahydrofuran and lithium bis-trimethylsilylamide or n-butyllithium, in a temperature range from −100° C. to +20° C., preferably from −75° C. to −40° C.

In addition, solvents employed for the individual steps are those mentioned above, preferably methylene chloride, dimethylformamide and 1,2-dimethoxyethane The acylation is in general carried out in one of the abovementioned ethers or halogenohydrocarbons, preferably tetrahydrofuran or methylene chloride, in a temperature range from −30° C. to 50° C., preferably from −10° C. to room temperature.

The compounds of the general formula (II) are new and can be prepared by reacting compounds of the general formula (VII)

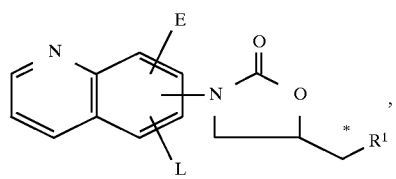

(VII)

in which

R$^1$, E and L have the meaning indicated above,
in one of the abovementioned solvents, preferably in methylene chloride, with oxidizing agents such as, for example, metachloroperbenzoic acid, hydrogen peroxide or peracetic acid, preferably with metachloroperbenzoic acid, in a temperature range from 0° C. to 80° C., preferably from 0° C. to 40° C.

The compounds of the general formula (VII) can be prepared by reacting, in analogy to the abovementioned process [C], compounds of the general formula (VIII)

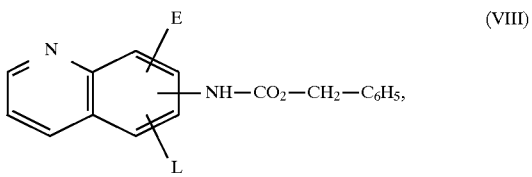

(VIII)

in which

E and L have the meaning indicated above,
with the epoxide of the formula (IV) and starting from the free hydroxyl function, likewise in analogy to the abovementioned compounds, introducing the group R$^1$.

The compounds of the general formulae (III), (V), (VI) and (VIII) are known per se or can be prepared by customary methods.

The compounds of the general formula (IV) are new and can be prepared by,
in known amines of the general formula (IX),

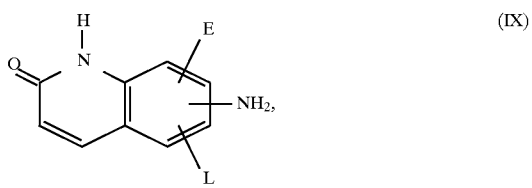

(IX)

in which

E and L have the meaning indicated above,
first protecting the free amino function with ClCO$_2$CH$_2$C$_6$H$_5$ in tetrahydrofuran at pH 10 and in a second step carrying out an alkylation (D'≠H) according to the conditions mentioned above.

The blocking of the free amino function is carried out in a temperature range from 150° C., to 200° C., preferably at 180° C. and normal pressure.

The compounds of the general formulae (I$a$)–(I$g$) are new and can each be prepared as described above.

The minimum inhibitory concentrations (MIC) there determined by the serial dilution method on Iso-Sensitest agar (Oxoid). For each test substance, a number of agar plates were prepared which, at twice the dilution in each case, contained falling concentrations of the active compound. The agar plates were inoculated using a multipoint inoculator (Denley). For inoculation, overnight cultures of the pathogenic organisms were used which had previously been diluted such that each inoculation point contained about 10$^4$ colony-forming particles. The inoculated agar plates were incubated at 37° C., and the microbial growth was read off after about 20 hours. The MIC ($\mu$g/ml) indicates the lowest active compound concentration at which it was not possible to detect growth using the naked eye.

| | | | MICs ($\mu$g/ml) | | | | |
|---|---|---|---|---|---|---|---|
| Ex. No. | Staph. 133 | Staph. 48N | Staph 25701 | Staph. 9TV | E. coli Neumann | Klebs. 57 USA | Psdm. Bonn |
| 3 | 2 | 2 | 2 | 1 | >64 | >64 | >64 |
| 4 | 4 | 8 | 4 | 2 | >64 | >64 | — |
| 5 | 16 | 16 | 16 | 8 | >64 | >64 | >64 |
| 7 | 8 | 8 | 8 | 2 | >32 | >32 | >32 |
| 12 | 8 | 8 | 8 | 4 | >64 | >64 | >64 |

For rapidly growing mycobacteria, the MIC determination was carried out following the method of broth microdilution described by Swenson [cf. J. M. Swenson, C. Thornberry, U. A. Silcox, Rapidly growing mycobacteria. Testing of susceptibility to 34 antimicrobial agents by broth microdilution. Antimicrobial Agents and Chemotherapy Vol. 22, 186–192 (1982)]. A deviation from this was the brain-heart extract medium treated with 0.1% by volume of Tween 80.

The mycobacterial strains used wvere ordered from DSM (German Collection of Microorganisms, Brunswick). They were incubated at 37° C. in a humid chamber.

The MICs were read off after 2–4 days when the preparation-free controls were cloudy as a result of growth. The MIC is defined as the lowvest preparation concentration which completely inhibits macroscopically visible growth.

| | MICs: Mycobacterium smegmatis | |
|---|---|---|
| Strain: | DSM 43061 | DSM 43465 |
| Inoculum [/ml] | 2.20U+04 | 3.10U+04 |
| Ex. No. | | |
| 3 | 2 | 8 |
| 4 | 4 | 8 |
| 6 | 8 | 4 |
| Isoniazide | 4 | 1 |
| Streptomycin | 4 | 4 |

The compounds of the general formulae (I), (Ia), (Ib), (Ic), (Id), (Ie), (If) and (Ig) have, combined with low toxicity, a wide antibacterial spectrum, especially against gram-positive bacteria and mycobacteria. Haemophilus influenzae and anaerobic microorganisms for rapidly growving mycobacteria. These properties make possible their use as chemotherapeutic active compounds in human and veterinary medicine.

The compounds according to the invention are particularly efficacious against bacteria and bacteria-like microorganisms such as mycoplasma. They are therefore particularly highly suitable for the prophylaxis and chemotherapy of local and systemic infections in human and veterinary medicine caused by such pathogenic organisms.

The present invention includes pharmaceutical preparations which, in addition to non-toxic, inert pharmaceutically suitable excipients, contain one or more compounds according to the invention or which consist of one or more active compounds according to the invention, and processes for the production of these preparations.

The active compound(s) can optionally also be present in microencapsulated form in one or more of the excipients indicated above.

Therapeutically active compounds should be present in the abovementioned pharmaceutical preparations in a concentration of approximately 0.1 to 99.5, preferably of approximately 0.5 to 95% by weight of the total mixture.

Apart from the compounds according to the invention, the abovementioned pharmaceutical preparations can also contain further pharmaceutical active compounds.

In general, it has proven advantaceous both in human and in veterinary medicine to administer the active compound(s) according to the intention in total amounts of approximately 0.5 to approximately 500, preferably 5 to 100, mg/kg of body weight every 24 hours, if appropriate in the form of several individual doses, to achieve the desired results. An individual dose contains the active compound(s) according to the invention preferably in amounts from approximately 1 to approximately 80, in particular 3 to 30, mg/kg of body weight.

For the purpose of widening the spectrum of action and in order to achieve an increase in action, the compounds according to the invention can also be combined wdith other antibiotics.

Appendix to the experimental section

| Abbreviations: | |
|---|---|
| Z | Benzyloxycarbonyl |
| Boc | tert-Butoxycarbonyl |
| DMF | Dimethylformamide |
| Ph | Phenyl |
| Me | Methyl |
| THF | Tetrahydrofuran |
| CDI | Carbonyldiimidazole |
| DCE | Dichloroetane |

Starting Compounds

EXAMPLE I

6-Benzyloxycarbonylamino-quinoline

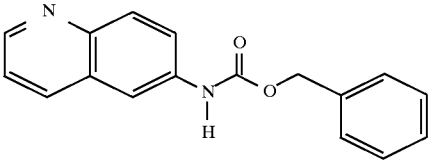

13.0 ml (76.28 mmol) of benzyl chloroformate are added dropwise in the course of 30 min to a stirred solution of 10.0 g (69.36 mmol) of 6-aminoquinoline in 160 ml of water and 80 ml of THF which is cooled to 0° C., pH=10 being maintained by simultaneous addition of a 4N NaOH solution. The mixture is stirred at 0° C. for a further 2 h, the THF is evaporated in vacuo and the residue is extracted 3 times with 50 ml of ethyl acetate. The combined organic extracts are dried over $MgSO_4$, the solvent is evaporated in vacuo and the residue is purified by chromatography on 450 g of silica gel (toluene:ethyl acetate 1:4), 11.60 g (60%) of the title compound are obtained as crystals.

Melting point: 122° C.; $R_f$=0.43 (toluene:ethyl acetate 1:4); MS (EI) m/z=278 (M⁻); ¹H-NMR (300 MHz, $D_6$-DMSO): δ=5.22 (s, 2H, $CH_2O$); 7.3–7.5 (m, 6H, Ph, quinoline-H); 7.78 (dd, J=1.5, 9 Hz, 1H, quinoline-H); 7.96 (d, J=9 Hz, 1H, quinoline-H); 8.17 (d, J=1.5 Hz, 1H, quinoline H-5); 8.25 (d, J=9 Hz, 1H, quinoline-H); 8.77 (m, 1H, quinoline H-2).

EXAMPLE II (5R)-3-(Quinolin-6-yl)-5-hydroxymethyl-oxazolidin-2-one

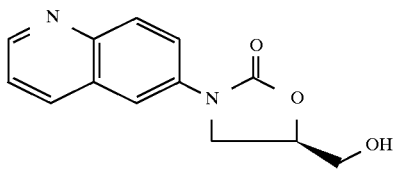

A stirred solution of 3.28 g (11.78 mmol of 6-benzyloxycarbonylamino-quinoline and 1 mg of 1,10-phenanthroline hydrate in 30 ml of anhydrous THF which is cooled to −78° C. is treated slowly with 4.70 ml (11.78 mmol) of a 2.5M solution of n-butyllithium in n-hexane until it changes colour. 1.67 ml (11.78 mmol) of (R)-glycidyl butyrate are then added dropwise and the reaction mixture is allowed to warm to room temperature in the course of 16 h. 30 ml of saturated aqueous $NH_4Cl$ solution are then added dropwise in the course of 15 min. The water phase is extracted 3 times with 60 ml of ethyl acetate, and the organic phases are combined, washed twice with 50 ml of NaCl solution and dried over $MgSO_4$. After evaporation of the solvent in vacuo, tritration of the residue with ether and recrystallization from 25 ml of ethanol, 1.30 g (45%) of the title compound are obtained as colourless crystals.

Melting point: 165° C.; $R_f$=0.08 (toluene:ethyl acetate 1:4); MS (DCI, $NH_3$) m/z=245 (M+H)⁺; ¹H-NMR (250 MHz, $D_6$-DMSO): δ=3.6–3.8 (m, 2H, $CH_2O$); 4.00 (dd, J=7, 10 Hz, 1H, H-4 trans); 4.25 (dd, J=10, 10 Hz, 1H, H-4 cis); 4.78 (m, 1H, H-5); 5.25 (t, J=6 Hz, 1H, OH); 7.52 (dd, J=4, 9 Hz, 1H, quinoline H-3); 7.92 (d, J=1.5 Hz, 1H, quinoline H-5); 8.02 (d, J=10 Hz, 1H, quinoline H-8); 8.3 (m, 2H, quinoline H-4.7); 8.82 (m, 1H, quinoline H-2).

EXAMPLE III (5R)-3-(5-Quinolin-6-yl)-5-methanesulphonyloxy-methyl-oxazolidin-2-one

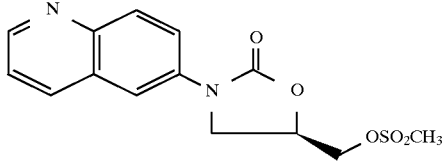

A stirred solution of 48.19 g (197 mmol) of the compound from Example II and 33 ml (236 mmol) of triethylamine in 300 ml of anhydrous dichloromethane which is cooled to 0° C. is slowly treated with 19.80 ml (256 mmol) of methane-sulphonyl chloride. The mixture is stirred at 0° C. for 10 min and stirred into 700 ml of ice-water. The organic phase is separated off, washed with 100 ml of saturated $NaHCO_3$ solution and 100 ml of ice-water and dried over $MgSO_4$. The solvent is evaporated in vacuo and the residue is stirred with 50 ml of ether, filtered off with suction and dried in a high vacuum. 46.0 g (72%) of the title compound are obtained as colourless crystals.

Melting point: 143° C.; $R_f$=0.14 (toluene:ethyl acetate 1:9); MS (DCI, $NH_3$) m/z=323 (M+H)⁺; ¹H-NMR (200 MHz, $D_6$-DMSO): δ=3.27 (s, 3H, $OSO_2CH_3$); 4.00 (dd, J=7, 10 Hz, 1H, H-4 trans); 4.36 (dd, J=10, 10 Hz, 1H, H-4 cis); 4.57 (m, 2H, $CH_2O$); 5.10 (m, 1H, H-5); 7.53 (dd, J=4, 9 Hz, 1H, quinoline H-3); 7.93 (d, J=1.5 Hz, 1H, quinoline H-5); 8.06 (d, J=10 Hz, 1H, quinoline H-8); 8.25 (dd, J=1.5, 10 Hz, 1H, quinoline H-7); 8.36 (d, J=9 Hz 1H, quinoline H-4); 8.84 (m, 1H, quinoline H-2).

EXAMPLE IV (5R)-3-(Quinolin-6-yl)-azidomethyl-oxazolidin-2-one

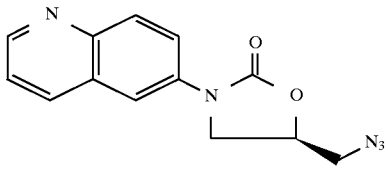

A stirred solution of 4.71 g (14.60 mmol) of the compound from Example III in 16 ml of anhydrous DMF is treated with 1.14 g (17.52 mmol) of sodium azide and stirred at 70° C. for 3 h. The mixture is allowed to cool to room temperature and is stirred into 50 ml of ice-water. The resulting precipitate is separated off by filtration, washed 3 times with 20 ml of water and dried in air. 3.50 g (89%) of the title compound are obtained as pale crystals.

Melting point: 92° C.; $R_f$=0.20 (toluene:ethyl acetate 1:9); MS (DCI, $NH_3$) m/z=270 (M+H)⁺; ¹H-NMR (250 MHz, $D_6$-DMSO): δ=3.71 (m, 2H, $CH_2N_3$); 3.95 (dd, J=6, 8 Hz, 1H, H-4 trans); 4.30 (dd, J=8, 8 Hz, 1H, H-4 cis); 4.98 (m, 1H, H-5); 7.52 (dd, J=9 Hz, 1H, quinoline H-3); 7.94 (d, J=1.5 Hz, 1H, quinoline H-5); 8.06 (d, J=10 Hz, 1H, quinoline H-8); 8.25 (dd, J=1.5, 10 Hz, 1H, quinoline H-7); 8.34 (d, J=9 Hz, 1H, quinoline H-4); 8.84 (m, 1H, quinoline H-2).

EXAMPLE V (5S)-3-(Quinolin-6-yl)-5-aminomethyl-oxazolidin-2-one dihydrochloride

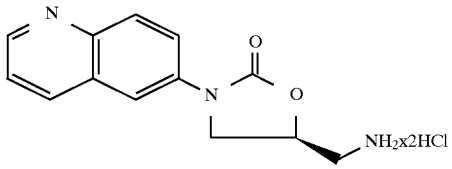

A stirred solution of 29.38 g (109 mmol) of the compound from Example IV in 80 ml of 1,2-dimethoxyethane is warmed to 50° C. 25 ml (130 mmol) of trimethyl phosphite are slowly added dropwise (evolution of gas) and the mixture is stirred at 90° C. for 2 hours after addition is complete. 3.3 ml of 6N HCl are then added dropwise and the mixture is stirred again at 100° C. for 6.5 h. It is allowed to cool to room temperature and the resulting oil is separated off. The oil is dissolved in a little acetonitrile, treated with 50 ml of toluene, concentrated in vacuo and dried over NaOH in a high vacuum. 30.5 g (99%) of the title compound are obtained. The hard foam is recrystallized from ethanol.

M.p.: 80° C. (dec.); $R_f$=0.37 (acetonitrile:water 4:1); MS (FAB) m/z=244 (M+H)⁺; ¹H-NMR (250 MHz, $D_6$-DMSO):

δ=3.35 (m, 2H, CH₂NH₂); 4.08 (dd, J=7, 9 Hz, 1H, H-4 trans); 4.39 (dd, J=9, 9 Hz, 1H, H-4 cis); 5.10 (m, 1H, H-5); 7.90 (dd, J=4, 9 Hz, 1H, quinoline H-3); 8.17 (d, J=1.5 Hz, 1H, quinoline H-5); 8.3–8.6 (m, 3H, quinoline H-8, 7.5); 8.90 (d, J=9 Hz, 1H, quinoline H-4); 9.10 (m, 1H, quinoline H-2).

EXAMPLE VI (5S)-3-(Quinolin-6-yl)-5-acetylaminomethyl-oxazolidin-2-one

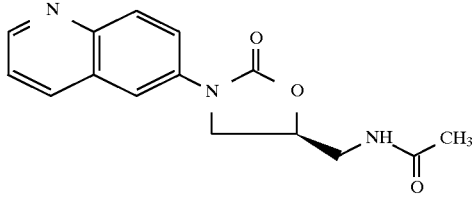

A stirred solution of 30.0 g (108 mmol) of the compound from Example V in 240 ml of THF is treated with a solution of 10 g of sodium hydroxide in 20 ml of water, a pH of 7.1 resulting. 11.6 ml (120 mmol) of acetic anhydride in 12 ml of THF are slowly added dropwise at 0°–5° C. to this and pH=9 is maintained by simultaneous addition of a 5N aqueous NaOH solution. The mixture is stirred at 0° C. for 1 h and the solvent is evaporated in vacuo. The residue is stirred well twice with 40 ml of water, separated off and dried in a high vacuum over Sicapent. 19.16 g (62%) of the title compound are obtained as colourless crystals.

M.p.: 146° C.; $R_f$=0.33 (dichloromethane:methanol 9:1); MS (FAB) m/z=286 (M+H)⁺; ¹H-NMR (250 MHz, D₆-DMSO): δ=1.85 (s, 3H, COCH₃); 3.50 (t, J=6.5 Hz, 2H, CH₂N); 3.90 (dd, J=7, 9 Hz, 1H, H-4 trans); 4.28 (dd, J=9, 10 Hz, 1H, H-4 cis); 4.80 (m, 1H, H-5); 7.52 (dd, J=4, 9 Hz, 1H, quinoline H-3); 7.88 (d, J=1.5 Hz, 1H, quinoline H-5); 8.05 (d, J=10 Hz, 1H, quinoline H-8) 8.25 (dd, J=1.5, 10 Hz, quinoline H-7); 8.34 (d, J=9 Hz, 1H, quinoline H-4); 8.82 (m, 1H, quinoline H-2).

EXAMPLE VII (5R)-3-(Quinolin-6-yl)-5-acetylaminomethyl-oxazolidin-2-one N-1-oxide

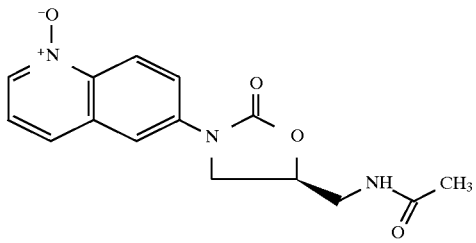

A stirred solution of 500 mg (1.75 mmol) of the compound from Example VI in 5 ml of dichloromethane is treated with 832 mg (3.85 mmol) of 80% strength m-chloroperbenzoic acid and stirred at room temperature for 16 h. The reaction mixture is then stirred into 20 ml of saturated aqueous Na₂CO₃ solution. The aqueous phase is separated off and evaporated in vacuo. 25 ml of toluene and 1.5 g of silica gel are added and the mixture is evaporated again. The residue is purified by chromatography on 50 g of silica gel (dichloromethane:methanol 4:1). The product-containing fractions are combined and treated with 200 ml of ether. The resulting precipitate is separated off by filtration and dried in a high vacuum. 453 mg (86%) of the title compound are obtained as colourless crystals.

M.p.: 191° C. (dec.); $R_f$=0.15 (dichloromethane:methanol 9:1); MS (FAB) m/z=302 (M+H)⁺; ¹H-NMR (300 MHz, D₆-DMSO): δ=1.85 (s, 3H, COCH₃); 3.50 (m, 2H, CH₂N); 3.91 (dd, J=7, 10 Hz, 1H, H-4 trans); 4.28 (dd, J=10, 10 Hz, 1H, H-4 cis); 4.82 (m, 1H, H-5); 7.3–7.5 (m, 2H); 7.9 (m, 1H); 8.0 (s, 1H, quinoline H-5); 8.3 (m, 1H); 8.50 (m, 1H, quinoline H-2).

PREPARATION EXAMPLES

Example 1

(5S)-3-(2-Oxo-1,2-dihydro-quinolin-6-yl)-5-acetylaminomethyl-oxazolidin-2-one

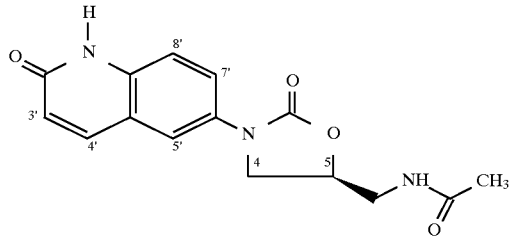

Method A:

A suspension of 2.73 g (9.10 mmol) of the N-oxide from Example VII and 2.59 g (13.59 mmol) of p-toluenesulphonyl chloride in 35 ml of chloroform is treated with 27.20 ml (27.20 mmol) of a 10% strength aqueous potassium carbonate solution and thorouohly stirred at room temperature for 4 h. The reaction mixture is then evaporated to dryness and chromatographed on 100 g of silica gel (acetonitrile:water 95:5). The product-containing fractions are collected, the solvent is evaporated in vacuo and the product obtained is dried in a high vacuum. 2.34 g (86% of theory) of the title compound are obtained as pale beige crystals.

M.p.: from 207° C. (dec.); $R_f$=0.40 (acetonitrile:water 9:1); MS (DCI, NH₃) m/z=302 (M+H)⁺; 319 (M+NH₄)⁺; ¹H-NMR (200 MHz, D₆-DMSO): δ=1.85 (s, 3H, CH₃CO); 3.42 (t, J=6.5 Hz, 2H, CH₂N); 3.78 (dd, J=7, 9 Hz, 1H, H-4 trans); 4.15 (dd, J=9, 10 Hz, 1H, H-4 cis); 4.75 (m, 1H, H-5); 6.52 (d, J=10 Hz, 1H, H-3'); 7.32 (d, J=10 Hz, 1H, H-4'); 7.73 (d, J=2 Hz, 1H, H-5'); 7.80 (dd, J=2, 10 Hz, 1H, H-7'); 7.91 (d, J=10 Hz, 1H, H-8; 8.27 (m, 1H, CONH); 11.73 (bs, 1H, NH).

Method B:

A stirred suspension of 652 mg (1.90 mmol) of the compound from Example 2 in 20 ml of anhydrous methanol is treated with 66 mg (0.20 mmol) of caesium carbonate and stirred at room temperature for 1 h. The solvent is evaporated in vacuo and the residue is stirred with 30 ml of ether. The precipitate is separated off by filtration. washed wiith 25 ml of water and 5 ml of ether and dried in a high vacuum. 358 mg (57%) of the title compound are obtained as pale crystals.

M.p.: 232°–233° C.

The other physical data are identical with the compound obtained by Method A.

Example 2

(5S)-5-[(Bisacetyl)aminomethyl]-3-(2-oxo-1,2-dihydro-quinolin-6-yl)-oxazolidin-2-one

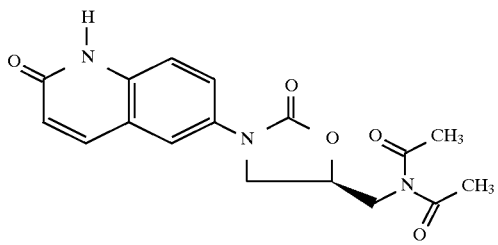

A stirred suspension of 5.45 g (10.53 mmol) of the anhydrous N-oxide from Example VII in 50 ml of acetic anhydride is heated at reflux for 24 h, a clear solution resulting. The mixture is allowed to cool and is concentrated to dryness on a rotary evaporator. The residue is treated with 30 ml of toluene and again concentrated to dryness. This process is repeated two more times, then the crude product is purified by filtration on 10 g of silica gel (dichloromethane:methanol 95:5) and by chromatography on 100 g of silica gel (acetonitrile:water 98:2). 1.84 g (58%) of the title compound are obtained.

M.p.: 135°–137° C.; $R_f$=0.33 (dichloromethane:methanol 9:1)/0.48 (acetonitrile:water 95:5); MS (DCI, NH$_3$) m/z= 344 (M+H)$^+$; $^1$H-NMR (200 MHz, D$^6$-DMSO): δ=2.38 (s, 6H, CH$_3$CO); 3.84 (dd, J=7, 9 Hz, 1H-H-4 trans); 4.10 (m, 2H, CH$_2$N); 4.20 (dd, J=9, 10 Hz, 1H, H-4 cis); 4.82 (m, 1H, H-5); 6.52 (d, J=10 Hz, 1H, H-3'); 7.33 (d, J=10 Hz, 1H, H-4'); 7.78 (m, 2H; H-5', H-7'); 7.92 (d, J=10 Hz, 1H, H-8'); 11.78 (bs, 1H, NH). IR (KBr): ν=3449, 1735, 1701, 1654, 1560, 1507, 1437 cm$^{-1}$.

Example 3

(5S)-3-(1-Methyl-2-oxo-1,2-dihydro-quinolin-6-yl)-5-acetylaminomethyl-oxazolidin-2-one

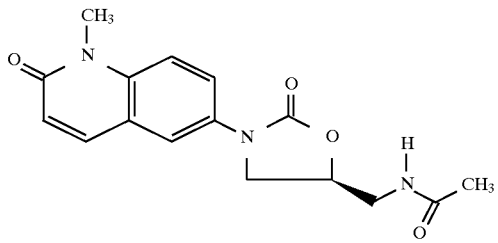

A suspension of 100 mg (0.33 mmol) of the compound from Example 1 and 1.36 mg (0.99 mnmol) of potassium carbonate in 4 ml of anhydrous DMF is treated with 67 μl (1.73 mmol) of iodomethane and stirred at 70° C. for 1 h. The reaction mixture is then concentrated to dryness, the residue is treated with a mixture of 20 ml of water and 10 ml of dichloromethane, the organic phase is separated off and the aqueous phase is extracted several times with dichloromethane. The combined extracts are dried over MgSO$_4$. The solvent is evaporated in vacuo, and the residue is purified by chromatography on 10 g of silica gel (dichloromethane:methanol 95:5). 60 mg (59%) of the title compound are obtained as colourless crystals.

M.p.: 252° C.; $R_f$=0.29 (dichloromethane:methanol 9:1); MS (DCI, NH$_3$) m/z=316 (M+H)$^+$; $^1$H-NMR (200 MHz, D$_6$-DMSO): δ=1.85 (s, 3H, CH$_3$CO); 3.44 (m, 2H CH$_2$N); 3.60 (s, 3H, NCH$_3$); 3.81 (dd, J=7, 9 Hz, 1H, H-4 trans); 4.17 (dd, J=9, 10 Hz, 1H, H-4 cis); 4.78 (m, 1H, H-5); 6.65 (d, J=10 Hz, 1H, H-3'); 7.59 (d, J=10 Hz, 1H, H-4'); 7.80 (d, J=1.5 Hz, 1H, H-5'); 7.92 (m, 2H, H-7', H-8'); 8.28 (t, J=6 Hz, 1H, CONH). IR (KBr): ν=3291, 1740, 1664, 1560, 1449, 1231, 1116, 812, 536 cm$^{-1}$.

As described for Example 3, the products listed in Table 1 are obtained by alkyation of the compound from Example 1 with the appropriate alkyl iodides:

TABLE 1

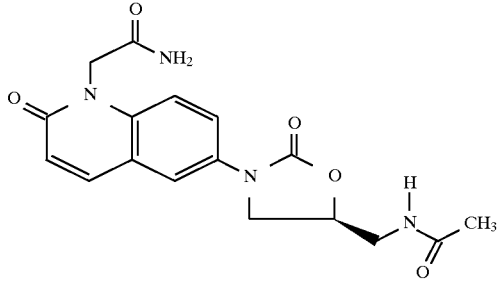

| Ex. No. | D | Yield (% of theory) | M.p. (°C.) | $R_f$ (CH$_2$Cl$_2$:MeOH) (ratio) | MS (DCI, NH$_3$), m/z (M + H)$^+$ |
|---|---|---|---|---|---|
| 4 | CH$_2$CH$_3$ | 45 | 196 | 0.39, (9:1) | 330 |
| 5 | CH(CH$_3$)$_2$ | 21 | 189 | 0.25, (95:5) | 344 |
| 6 | CH$_2$CN$^{a)}$ | 32 | 185 | 0.13, (9:1) | 341 |
| 7 | CH$_2$CH$_2$OH | 51 | 174 | 0.57, (85:15) | 346 |
| 8 | CH$_2$Ph$^{b)}$ | 26 | 129 | 0.28, (9:1) | 392 |

$^{a)}$using ClCH$_2$CN
$^{b)}$using BrCH$_2$Ph

Example 9

(5S)-3-(1-[Acetamido-2-yl]-2-oxo-1,2-dihydro-quinolin-6-yl)-5-acetylaminomethyl-oxazolidin-2-one A solution of 10 mg (0.03 mmol) of the cyano compound from Example 5 in 0.2 ml of acetone is treated with 60 μl (0.06 mmol) of a 1M aqueous potassium carbonate solution and with 40 μl (0.18 mmol) of 30% H$_2$O$_2$ and is stirred at room temperature for 2 h. The reaction mixture is then treated with 1 ml of toluene and evaporated to dryness in vacuo, and the residue is purified by chromatography on 1 g of silica gel (dichloromethane:methanol 95:5). 7.2 mg (66%) of the title compound are obtained as colourless crystals.

$R_f$=0.11 (dichloromethane:methanol 9:1); MS (DCI, NH$_3$) m/z=359 (M+H)$^+$, 376 (M+NH$_4$)$^+$; $^1$H-NMR (200 MHz, D$_6$-DMSO): δ=185 (s, 3H, COCH$_3$); 3.45 (m, 2H CH$_2$N); 3.79 (dd, J=6, 9 Hz, 1H, H-4 trans); 4.18 (dd, J=9, 10 Hz, 1H, H-4 cis); 4.77 (m, 1H, H-5); 4.88 (s, 2H, NCH$_2$CON); 6.65 (d, J=10 Hz, 1H, H-3'); 7.27 (bs, 1H, CONH$_2$); 7.32 (d, J=10 Hz, 1H, H-4'); 7.70 (bs, 1H, CONH$_2$); 7.85 (m, 2H, H-5', H-7'); 7.96 (d, J=10 Hz, 1H, H-8'); 8.28 (t, J=6.5 Hz, 1H, CO<u>NH</u>CH$_2$).

Example 10

(5S)-3-(1-Hydroxymethyl-2-oxo-1,2-dihydro-quinolin-6-yl)-5-acetaminomethyl-oxazolidin-2-one

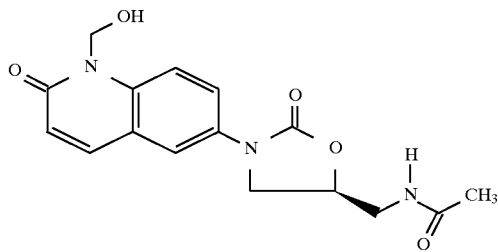

A stirred suspension of 100 mg (0.33 mmol) of the compound from Example 1 in 3.3 ml (3.3 mmol) of 30% strength aqueous formalin solution is heated to reflux for 2 h. It is then evaporated to dryness in vacuo, and the residue is treated with 10 ml of toluene and evaporated again. The residual solid is triturated with 5 ml of ether, filtered off with suction and dried in a high vacuum. 104 mg (95%) of the title compound are obtained as a pale powder.

Example 11

(5S)-3-(1-N,N-[Dimethylamino-methyl]-2-oxo-1,2-dihydro-quinolin-6-yl)-5-acetaminomethyl-oxazolidin-2-one

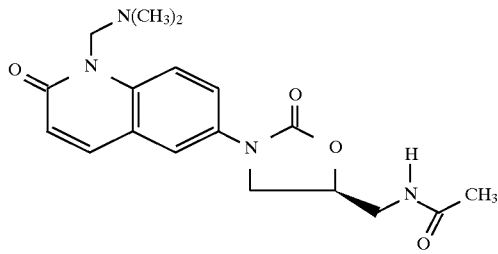

500 mg (0.48 mmol) of the compound from Example 1 are dissolved in 5 ml of hot ethanol, treated with 0.36 ml of 30% strength aqueous formalin solution and 46 μl (0.53 mmol) of 51% strength aqueous dimethylamine solution and heated to reflux for 8 h. Working up was carried out as described for Example 9. 139 mg (81%) of the title compound are obtained as a solid.

Example 12

(5S)-3-(1-Methanesulphonyl-2-oxo-1,2-dihydro-quinolin-6-yl)-5-acetylaminomethyl-oxazolidin-2-one

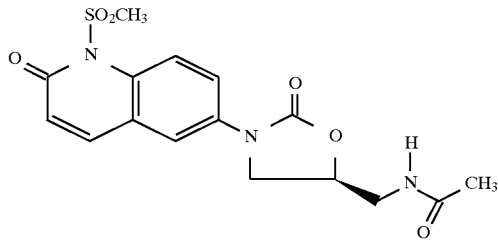

A stirred solution of 100 mg (0.33 mmol) of the compound from Example 1 and 0.56 ml (3.96 mmol) of triethylamine in 10 ml of anhydrous dichloromethane which is cooled to 0° C. is slowly treated with 0.27 ml (3.44 mmol) of methanesulphonyl chloride. The mixture is stirred for 4 h at 20° C. and stirred into 5 ml of ice-water. The organic phase is separated off, washed with 5 ml of saturated $NaHCO_3$ solution and dried over $MgSO_4$. The solvent is evaporated in vacuo and the residue is purified by chromatography on 5 g of silica gel (dichloromethane:methanol 95:5). 224 mg (20%) of the title compound are obtained as colourless crystals.

M.p.: 171°–173° C.; $R_f$=0.72 (acetonitrile:water 95:5); MS (FAB) m/z=380 (M+H)$^+$, 402 (M+Na)$^+$; $^1$H-NMR (200 MHz, $D_6$-DMSO): δ=1.84 (s, 3H, $COCH_3$); 3.48 (t, J=6 Hz, 2H $CH_2N$); 3.79 (s, 3H, $CH_3SO_2$); 3.90 (dd, J=7, 9 Hz, 1H, H-4 trans); 4.27 (dd, J=9, 9 Hz, 1H, H-4 cis); 4.80 (m, 1H, H-5); 7.42 (d, J=10 Hz, 1H, H-3'); 8.03 (m, 2H, H-4', H-5'); 8.30 (m, 7H, H-7', CO<u>NH</u>); 8.59 (d, J=10 Hz, 1H, H-8'). IR (KBr): ν3338, 1734, 1654, 1600, 1549, 1517, 1654, 1170, 1140, 986, 813, 528 cm$^{-1}$

Example 13

(5S)-3-(1-[3-Chlorobenzoyl]-2-oxo-1,2-dihydro-quinolin-6-yl)-acetaminomethyl-oxazolidin-2-one

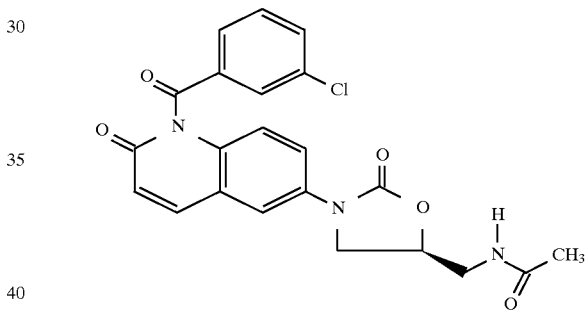

175 mg (1.00 mmol) of 3-chlorobenzoyl chloride are added slowly to a stirred solution of 150 mg (0.50 mmol) of the compound from Example 1 and 0.21 ml (1.50 mmol) of triethylamine in 5 ml of anhydrous DMF which is cooled to 0° C. The mixture is stirred for 2 h at 0° C. and diluted with 20 ml of wxater and 50 ml of dichloromethane, the organic phase is separated off, the aqueous phase is extracted several times with 5 ml of dichloromethane and the combined organic extracts are dried over $MgSO_4$. After evaporating the solvent in vacuo, purifying the crude product by chromatography on 15 g of silica gel (dichloromethane:methanol 95:5) and tritrating the residue with ether, 95 mg (43%) of the title compound are obtained as crystals.

M.p.: 172°–174° C.; $R_f$=0.47 (dichloromethane:methanol 9:1); MS (DCI, $NH_3$): m/z=440 (M+H)$^+$; $^1$H-NMR (300 MHz, $D_6$-DMSO): δ=1.86 (s, 3H, $COCH_3$); 3.50 (t, J=6 Hz, 2H $CH_2N$); 3.92 (dd, J=7, 9 Hz, 1H, H-4 trans); 4.30 (dd, J=9, 10 Hz, 1H, H-4 cis); 4.82 (m, 1H, H-5); 7.56 (d, J=10 Hz, 1H, H-3'); 7.65–8.35 (m, 8H, H-arom., CONH); 8.58 (d, J=9 Hz, 1H, H-8'); IR (KBr): ν=3284, 1740, 1654, 1560, 1517, 1424, 1258, 1216, 888, 740 cm$^{-1}$

Example 14

(5S)-5-(N-Acetyl,N-(2-cyanoethyl)aminomethyl-3-
(2-oxo-1,2-dihydro-quinolin-6-yl)-oxazolidin-2-one

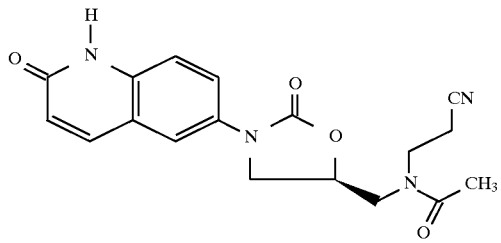

100 mg (0.33 mmol) of the compound from Example 1 are added in portions to a stirred suspension of 16 mg (0.40 mmol) of sodium hydride (60% in oil) in 2 ml of azhydrous DMF which is cooled to 0° C. and the mixture is stirred until evolution of hydrogen has ended. 65 µl (0.99 mmol) of acrylonitrile are added dropwise to the resulting clear solution in the course of 5 min. The cooling bath is removed, and after 15 min the reaction is terminated by addition of 1 ml of 1N citric acid. The reaction mixture is poured into a mixture of 10 ml of dichloromethane and 5 ml of water and thoroughly stirred. The organic phase is separated off, the water phase is extracted several times with 5 ml of dichloromethane and the combined extracts are dried over MgSO$_4$. The solvent is evaporated in vacuo and the residue is purified by chromatography on 5 g of silica gel (dichloromethane:methanol 95:5). 30 mg (26%) of the title compound are obtained as colourless crystals.

M.p.: 124°–125° C.; R$_f$=0.17 (dichloromethane:methanol 9:1); MS (FAB) m/z=355 (M+H)$^+$; $^1$H-NMR (250 MHz, D$_6$-DMSO): δ=2.08, 2.12 (s, 3H, COCH$_3$); 2.70–2.90 (m, 2H, CH$_2$CN); 3.5–3.9 (m, 5H, CH$_2$N, H-4 trans); 4.15 (dd, J=9, 10 Hz, 1H, H-4 cis); 4.90 (m, 1H-5); 6.52 (d, J=10 Hz, 1H-3'); 7.31 (d, J=10 Hz, 1H-4'); 7.80 (m,2H, H-5', H-7'); 7.91 (dd, J=2, 10 Hz, 1H, H-8'); 11.90 (bs, 1H, NH).

The Michael adduct described in Table 2 is obtained in analogy to Example 14:

TABLE 2

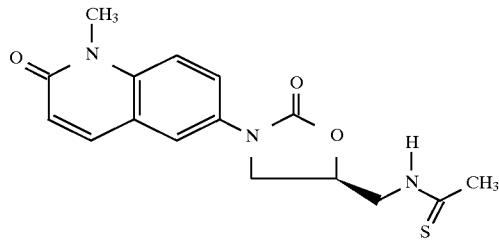

| Ex. No. | R$^{33}$ | Yield (% of theory) | R$_f$/Eluent (ratio) | MS (FAB), m/z (M + H)$^+$ |
|---|---|---|---|---|
| 15 | COOCH$_3$ | 18 | 0.14, I(9:1) | 388 |

Example 16

(5S)-3-(1-[N,N'-Dimethyl-ureido-carbonyl]-2-oxo-1,2-dihydro-
quinolin-6-yl)-5-acetylaminomethyl-oxazolidin-2-one

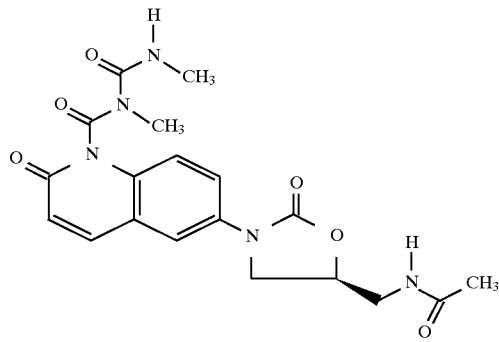

A suspension of 100 mg (0.33 mmol) of the compound from Example 1 in 1.8 ml of DMF is treated with 0.58 ml (10.0 mmol) of methyl isocyanate and 0.69 ml (5.0 mmol) of triethylamine and stirred at 50° C. for 100 h. The reaction mixture is then allowed to cool and the volatile constituents are removed in vacuo. The residue is purified by chromatography on 25 g of silica gel (dichloromethane:methanol 95:5). The product-containing fractions are collected and the solvent is evaporated in vacuo. The residue is dissolved in 0.2 ml of dichloromethane:methanol 95:5 and precipitated by slow addition of 2 ml of ether and 2 ml of pentane. 22 mg (19%) of the title compound are obtained as pale crystals.

M.p.: from 112° C. (dec.); R$_f$=0.14 (dichloromethane:methanol 9:1); MS (FAB) m/z=416 (M+H)$^+$, 438 (M+Na)$^+$; $^1$H-NMR (200 MHz, D$_6$-DMSO): δ=1.85 (s, 3H, COCH$_3$); 2.85 (m, 3H, CH$_3$N); 2.96 (s, 3H, CH$_3$N); 3.44 (t, J=5 Hz, 2H, CH$_2$N); 3.81 (dd, J=6, 9 Hz, 1H, H-4 trans); 4.19 (dd, J=9, 10 Hz, 1H, H-4 cis); 4.78 (m, 1H, H-5); 5.73 (bs, 1H, CO<u>NH</u>CH); 6.72 (d, J=10 Hz, 1H, H-3'); 7.30 (d, J=10 Hz, H-4'); 7.90 (m, 2H, H-5', H-7'); 8.12 (d, J=10 Hz, 1H, H-8'); 8.28 (t, J=6 Hz, 1H, CO<u>NH</u>CH$_2$).

Example 17

(5S)-3-(1-Methyl-2-oxo-1,2-dihydro-quinolin-6-yl)-
5-thioacetylaminomethyl-oxazolidin-2-one A stirred solution of 125 mg (0.40 mmol) of the compound from Example 3 and 162 mg (0.40 mmol) of Lawesson's reagent in 5 ml of anhndrous 1,2-dimethoxyethane was heated at 100° C. for 2 h. The reaction mixture as then allowed to cool, 20 g of silica gel were added and the solvent was evaporated in vacuo. The residue was added to a column and purified by chromatography on 200 g of silica gel (ethyl acetate). 22 mg (17%) of the title compound were obtained as pale crystals.

M.p.: 158°–160° C.; R$_f$=0.46 (dichloromethane:methanol 9:1); MS (DCI, NH$_3$) m/z=332 (M+H)$^+$; $^1$H-NMR (200

MHz, D$_6$-DMSO): δ=2.45 (s, 3H, CH$_3$CS); 3.61 (s, 3H, NCH$_3$); 3.8–4.0 (m, 3H, CH$_2$N, H-4 trans); 4.22 (dd, J=9, 10 Hz, 1H, H-4 cis); 5.00 (m, 1H, H-5); 6.65 (d, J=10 Hz, 1H, H-3); 7.58 (d, J=10 Hz, 1H, H-4'); 7.82 (d, J=1.5 Hz, 1H, H-5'); 7.9 (m, 2H, H-7', H-8'); 10.41 (bt, 1H, CONH).

We claim:

1. An oxazolidinone compound of the formula (I)

[Structural formula (I) depicting a bicyclic ring system with substituents A, D, E, L attached, and an oxazolidinone group with R$^1$]

in which

A represents an oxygen or a sulphur atom,

D represents hydrogen or cycloalkyl having 3 to 6 carbon atoms, or represents straight-chain or branched alkooxycarbonyl having up to 4 carbon atoms, or represents straight-chain or branched alkyl or alkenyl each having up to 9 carbon atoms, which is optionally substituied by cyano, trifluoromethyl, halogoen, hydroxyl, pyridyl, phenyl, carboxyl, carboxamido, straight-chain or branched alkoxycarbonyl having up to 5 carbon atoms, naphthyl, cycloalkyl having 3 to 6 carbon atoms, and/or by a group of the formula

—(CO)$_3$—NR$^2$R$^3$, R$^4$—N—SO$_2$—R$^5$,

R$^6$R$^7$—N—SO$_2$— or R$^8$—S(O)$_b$, in which a denotes a number 0 or 1,

R$^2$, R$^3$R$^4$, R$^6$ and R$^7$ are identical or different and denote hydrogen, straight-chain or branched alkyl having up to 5 carbon atoms or phenyl, b denotes a number 0, 1 or 2, R$^5$ and R$^8$ are identical or different and denote straight-chain or branched alkyl having up to 6 carbon atoms, benzyl, phenyl or tolyl, or D represents straight-chain or branched acyl having up to 5 carbon atoms, which is optionally substituted by trifluoromethyl, trichloromethyl or a group of the formula —OR$^9$, in which R$^9$ denotes hydrogen or straight-chain or branched alkyl having up to 5 carbon atoms, which is optionally substituted by phenyl or naphthyl, or D represents a group of the formula —(CT)$_d$—NR$^{10}$R$^{11}$, —(CO)$_e$—NR$^{12}$—CO—NR$^{13}$R$^{14}$, —NR$^{15}$—SO$_2$R$^{16}$, R$^{17}$R$^{18}$—N—SO$_2$, —R$^{19}$—S(O)$_f$ or —CO—R$^{20}$, in which T denotes an oxygen or sulplur atom, d and e are identical or different and have the meaning of a indicated above, R$^{10}$, R$^{11}$, R$^{12}$, R$^{13}$, R$^{14}$, R$^{15}$, R$^{17}$ and R$^{18}$ have the meaning of R$^2$, R$^3$ and R$^4$ in each case indicated above, f is the meaning of b indicated above, R$^{16}$ and R$^{19}$ are identical or different and have the meaning of R$^5$ and R$^8$ indicated above, R$^{20}$ denotes aryl having 6 to 10 carbon atoms, which is optionally substituted by halogen, E and L are identical or different and represent hydrogen, carboxyl, halogen, cyano, formyl, trifluoromethyl, nitro, or represent straight-chain or branched alkyl having up to 4 carbon atoms, R$^1$ represents azido, hydroxyl or a group of the formula —OR$^{21}$, O—SO$_2$R$^{22}$ or —NR$^{23}$R$^{24}$, in which R$^{21}$ denotes straight-chain or branched acyl having up to 6 carbon atoms or benzy, R$^{22}$ denotes straight-chain or branched alkyl, having up to 5 carbon atoms, phenyl or tolyl, R$^{23}$ and R$^{24}$ are identical or different and denote cycloalkyl having 3 to 6 carbon atoms, hydrogen, phenyl or straight-chain or branched alkoxy haing up to 6 carbon atoms, tert-butoxycarbonyl, fluorenyloxycarbonyl or benzyloxycarbonyl, or denote straight-chain or branched alkyl having up to 6 carbon atoms, which is optionally substituted by cyano or alkoxycarbonyl having up to 4 carbon atoms, or R$^{23}$ and/or R$^{24}$ denotes a group of the formula —CT'—R$^{25}$, P(O)(OR$^{26}$)(OR$^{27}$) or —SO$_2$—R$^{28}$, in which T' has the meaning of T indicated above, R$^{25}$ denotes cycloalkyl having 3 to 6 carbon atoms, trifluoromethyl or straight-chain or branched alkoxy having up to 6 carbon atoms, phenyl, benzyloxy or hydrogen, or denotes straight-chain or branched alkyl having up to 6 carbon atoms, which is optionally substituted by straight-chain or branched alkoxycarbonyl having up to 5 carbon atoms, cyano, fluorine, chlorine, bromine or trifluoromethyl, or denotes straight-chain or branched thioalkyl or acyl each having up to 5 carbon atoms, or denotes a group of the formula —NR$^{29}$R$^{30}$, in which R$^{29}$ and R$^{30}$ are identical or different and denote hydrogen, phenyl or straight-chain or branched alkyl having up to 4 carbon atoms, or R$^{26}$ and R$^{27}$ are identical or different and denote hydrogen or straight-chain or branched alkyl having up to 4 carbon atoms, R$^{28}$ denotes straight-chain or branched alkyl having up to 4 carbon atoms or phenyl, or a salt thereof or a stereoisomer of said compound or salt.

2. A compound of the formula (I) according to claim 1 in which

A represents an oxygen or a sulphur atom,

D represents hydrogen, cyclopropyl, cyclopentyl or cyclohexyl, or represents straight-chain or branched alkoxycarbonyl having up to 3 carbon atoms, or represents straight-chain or branched alkyl or alkenyl each having up to 6 carbon atoms, which is optionally substituted by cyano, trifluoromethyl, fluorine, chlorine, bromine, hydroxyl, pyridyl, phenyl, carboxyl, carboxamido, straight-chain or branched alkoxycarbonyl having up to 4 carbon atoms, naphthyl, cyclopropyl, cyclopentyl or cyclohexyl and/or by a group of the formula —(CO)$_a$—NR$^2$R$^3$, R$^4$—N—SO$_2$—R$^5$, R$^6$R$^7$—N—SO$_2$— or R$^8$—S(O)$_b$, in which a denotes a number 0 or 1, R$^2$,R$^3$, R$^4$, R$^6$ and R$^7$ are identical or different and denote hydrogen, straight-chain or branched alkyl having up to 3 carbon atoms or phenyl, b denotes a number 0, 1 or 2, R$^5$ and R$^8$ are identical or different and denote straight-chain or branched alkyl having up to 4 carbon atoms, benzyl, phenyl or tolyl, or D represents straight-chain or branched acyl having up to 4 carbon atoms, which is optionally substituted by trifluoromethyl, trichloromethyl or a group of the formula —$OR^9$,
in which
$R^9$ denotes hydrogen or straight-chain or branched alkyl having up to 4 carbon atoms, which is optionally substituted by phenyl or naphthyl, or
D represents a group of the formula —$(CT)_d$—$NR^{10}R^{11}$, —$(CO)_e$—$NR^{12}$—CO—$NR^{13}R^{14}$, —$NR^{15}$—$SO_2R^{16}$, $R^{17}R^{18}$—N—$SO_2$—, $R^{19}$—$S(O)_f$ or —CO—$R^{20}$,
in which
T denotes an oxygen or sulphur atom,
d and e are identical or different and have the meaning of a indicated above,
$R^{10}$, $R^{11}$, $R^{12}$, $R^{13}$, $R^{14}$, $R^{15}$, $R^{17}$ and $R^{18}$ have the meaning of $R^2$, $R^3$ and $R^4$ in each case indicated above,
f has the meaning of b indicated above,
$R^{16}$ and $R^{19}$ are identical or different and have the meaning of $R^5$ and $R^8$ indicated above,
$R^{20}$ denotes phenyl or naphthyl, which is optionally substituted by fluorine, chlorine or bromine,
E and L are identical or different and represent hydrogen, fluorine, chlorine, bromine, cyano, methyl or trifluoromethyl,
$R^1$ represents azido, hydroxyl or a group of the formula —$OR^{21}$, O—$SO_2R^{22}$ or —$NR^{23}R^{24}$,
in which
$R^{21}$ denotes straight-chain or branched acyl having up to 5 carbon atoms or benzyl,
$R^{22}$ denotes straight-chain or branched alkyl having up to 4 carbon atoms, phenyl or tolyl,
$R^{23}$ and $R^{24}$ are identical or different and denote cyclopropyl, cyclopentyl, cyclohexyl, hydrogen, phenyl or straight-chain or branched alkoxy having up to 5 carbon atoms, tert-butoxycarbonyl or benzyloxycarbonyl, or denote straight-chain or branched alkyl having up to 4 carbon atoms, which is optionally substituted by cyano or by straight-chain or branched alkoxycarbonyl having up to 3 carbon atoms, or
$R^{23}$ and/or $R^{24}$ denotes a group of the formula —CT'—$R^{25}$, P(O)($OR^{26}$)($OR^{27}$) or —$SO_2$—$R^{28}$,
in which
T' has the meaning of T indicated above,
$R^{25}$ denotes cyclopropyl, cyclopentyl, cyclohexyl, trifluoromethyl or straight-chain or branched alkoxy having up to 5 carbon atoms, phenyl, benzyloxy or hydrogen, or denotes straight-chain or branched alkyl having up to 5 carbon atoms, which is optionally substituted by straight-chain or branched alkoxycarbonyl having up to 4 carbon atoms, cyano, fluorine, chlorine, bromine or trifluoromethyl, or denotes straight-chain or branched thioalkyl or acyl each having up to 4 carbon atoms, or denotes a group of the formula —$NR^{29}R^{30}$,
in which
$R^{29}$ and $R^{30}$ are identical or different and denote hydrogen, phenyl or straight-chain or branched alkyl having up to 3 carbon atoms,
$R^{26}$ and $R^{27}$ are identical or different and denote hydrogen or straight-chain or branched alkyl having up to 3 carbon atoms, $R^{28}$ denotes straight-chain or branched alkyl having up to 3 carbon atoms or phenyl,
or a salt thereof or a stereoisomer of said compound or salt.

3. A compound of the formula (I) according to claim 1 in which

A represents an oxygen or a sulphur atom,
D represents hydrogen, cyclopropyl, cyclopentyl, cyclohexyl, allyl or straight-chain or branched alkyl having up to 5 carbon atoms, which is optionally substituted by cyano, hydroxyl, trifluoromethyl, fluorine, chlorine, phenyl, carboxyl, carboxamido, straight-chain or branched alkoxycarbonyl having up to 3 carbon atoms, cyclopropyl, cyclopentyl or cyclohexyl and/or by a group of the formula —$(CO)_a$—$NR^2R^3$, $R^4$—N—$SO_2$—$R^5$, $R^6R^7$N—$SO_2$— or $R^8$—$S(O)_b$,
in which
a denotes a number 0 or 1,
$R^2$, $R^3$, $R^4$, $R^6$ and $R^7$ are identical or different and denote hydrogen or methyl,
b denotes a number 0, 1 or 2,
$R^5$ and $R^8$ are identical or different and denote straight-chain or branched alkyl having up to 3 carbon atoms, benzyl, phenyl or tolyl, or
D represents a group of the formula —$(CT)_d$—$NR^{10}R^{11}$, —$(CO)_e$—$NR^{12}$—CO—$NR^{13}R^{14}$, —$NR^{15}$—$SO_2R^{16}$, $R^{17}R^{18}$N—$SO_2$—, $R^{19}$—$S(O)_f$ or —CO—$R^{20}$,
in which
T denotes an oxygen or sulphur atom,
d and e are identical or different and have the meaning of a indicated above,
$R^{10}$, $R^{11}$, $R^{12}$, $R^{13}$, $R^{14}$, $R^{15}$, $R^{17}$ and $R^{18}$ have the meaning of $R^2$, $R^3$ and $R^4$ in each case indicated above,
f has the meaning of b indicated above,
$R^{16}$ and $R^{19}$ are identical or different and have the meaning of $R^5$ and $R^8$ indicated above,
$R^{20}$ denotes phenol or naphthyl which is optionally substituted by fluorine, chlorine or bromine,
E and L are identical or different and represent hydrogen or fluorine,
$R^1$ represents azido, hydroxyl or a group of the formula —$OR^{21}$, O—$SO_2R^{22}$ or —$NR^{23}R^{24}$,
in which
$R^{21}$ denotes straight-chain or branched acyl having up to 4 carbon atoms,
$R^{22}$ denotes methyl or tolyl,
$R^{23}$ and $R^{24}$ are identical or different and denote cyclopropyl, hydrogen, phenyl or straiqht-chain or branched alkoxy having up to 4 carbon atoms, tert-butoxycarbonyl or benzyloxycarbonyl, or denote straight-chain or branched alkyl having up to 3 carbon atoms, which is optionally substituted by cyano or methoxycarbonyl, or
$R^{23}$ and/or $R^{24}$ denotes a group of the formula —CT'—$R^{25}$,
in which
T' has the meaning of T indicated above,
$R^{25}$ denotes cyclopropyl, cyclopentyl, cyclohexyl, trifluoromethyl or straight-chain or branched alkoxy having up to 4 carbon atoms, phenyl, benzyloxy or hydrogen, or denotes straight-chain or branched alkyl having up to 4 carbon atoms, which is optionally substituted by straight-chain or branched alkoxycarbonyl having up to 3 carbon atoms, cyano, fluorine, chlorine, bromine or trifluoromethyl, or denotes straight-chain or branched thioalklyl or acyl each having up to 3 carbon atoms, or denotes a group of the formula —NR$^{29}$R$^{30}$, in which R$^{29}$ and R$^{30}$ are identical or different and denote hydrogen, phenyl, methyl or ethyl, or a salt thereof or a stereoisomer of said compound or salt.

4. A compound of the formula (I) according to claim 1 in which

E and L represent hydrogen and the oxazolidinone radical is bonded to the 1,2-dihydroquinolinyl ring in position 6 or 7.

5. A pharmaceutical composition with comprises a compound or salt thereof according to claim 1 and pharmaceutically suitable excipient.

6. A method of treating microbial infections to a host in need thereof which comprises administering an antimicrobicidally effective amount of a compound or salt thereof according to claim 1 to said host.

* * * * *